United States Patent [19]

Kandul et al.

[11] 4,073,809
[45] Feb. 14, 1978

[54] METHOD FOR PRODUCING TRIALKYLPHOSPHINE OXIDES

[76] Inventors: Jury Vasilievich Kandul, bulvar Lesi Ukrainki, 8, kv. 3; Valery Yakovlevich Semeny, ulitsa A.Navoi, 57, kv. 27; Mikhail Danilovich Pivovarov, ulitsa Sh.Aleikhema, 19, kv. 68; Vladlen Vasilievich Malovik, ulitsa A.Malyshko, 33, kv. 125; Ivan Karpovich Mazepa, ulitsa A.Dovbusha, 12; Ninel Gavrilovna Feschenko, ulitsa E.Potie, 11, kv. 67, all of, Kiev, U.S.S.R.

[21] Appl. No.: 689,980

[22] Filed: May 26, 1976

[51] Int. Cl.$^2$ .............................................. C07F 9/53
[52] U.S. Cl. ............................................ 260/606.5 P
[58] Field of Search .................................. 260/606.5 P

[56] References Cited
PUBLICATIONS

Chemical Abstracts, V71, 124582b (1969).
Chemical Abstracts, V55, 6418i (1961).
Kasolapoff, Organic Phosphorus Compounds, Wiley--Interscience, N.Y., pp. 374 to 379 (1972).

Primary Examiner—Helen M. S. Sneed
Attorney, Agent, or Firm—Haseltine, Lake & Waters

[57] ABSTRACT

The method for producing trialkylphosphine oxides having the general formula $R_3PO$, where R is an alkyl having from 1 to 16 carbon atoms, consists in that red phosphorus reacts with an alkyl iodide in the presence of a catalyst — iodine or hexaalkyliodophosphorane-phosphonium pentaiodide — while gradually adding alkyl iodide to the reaction mixture, and maintaining the reaction temperature at 180° – 230° C, with subsequent isolation of the end product.

The proposed method simplifies the process for preparing trialkylphosphine oxides, increases the yield of the end product to 80 – 90 per cent by weight, rules out side reactions of dehydrohalogenation of alkyl iodides, and also shortens the process to 8 – 10 hours.

3 Claims, No Drawings

METHOD FOR PRODUCING TRIALKYLPHOSPHINE OXIDES

This invention relates to producing organophosphoric compounds, and more particularly it relates to a method of producing trialkylphosphine oxides that are widely used as complexing agents, additives to lubricants, antipyrenes, and also as intermediates for the synthesis of various organophosphorus compounds.

A method is known in the art for producing oxides of lower trialkylphosphines ($C_1$–$C_5$) by the reaction of the corresponding alkyl iodides with red phosphorus taken in the molar ratio of 3:1.5 in the presence of catalytic quantities of iodine. The process is effected in a sealed tube or in an autoclave with stirring, at a temperature of 200°–240° C and a pressure of 25–50 atm in the course of 4–8 hours. The yield of trialkylphosphine oxides is 25–75 percent by weight.

The disadvantage inherent in the known method is that the process pressure is high, which involves the necessity of using autoclaves. The capacity of autoclaves is limited, and since the reaction is exothermic, the reaction mass inside large autoclaves is overheated, the end products are tarred, and their yield is reduced.

Moreover, the process requires quite complicated equipment.

Also known is a method for producing higher trialkylphosphine oxides (over 5 carbon atoms) in which the appropriate alkyl iodides are heated with phosphorus diiodide, or with red phosphorus in the presence of catalytic quantities of iodine (10–15 percent by weight with respect to the theoretically required quantity) at a temperature of 145°–210° C. The synthesis is continued for 30 hours with hexyl iodide and 80–100 hours with iso-amyl iodide.

The yield of the end product is 50–75 percent by weight.

The disadvantage of this method is the length of the process, the low yields (50–75 percent), and the impossibility of obtaining lower trialkylphosphine oxides ($C_1$–$C_4$) under these conditions.

Furthermore, a method is known for preparing triisoamylphosphine oxides and tributylphosphine oxides by adding 0.52 mole of hexaisoamyl- or hexa-n-octyliodophosphoranphosphonium pentaiodides per gram-atom of red phosphorus and 3 g-mole of alkyl iodide. The process is continued for 30–50 hours.

In all processes known in the prior art, the required quantities of the reagents are charged at one time, and the reaction mixture is then heated. As this quantity of alkyl iodide is heated, hydrogen iodide is partly split off to form unsaturated compounds. For example, trimethylethylene is formed in the case with iso-amyl iodide as follows:

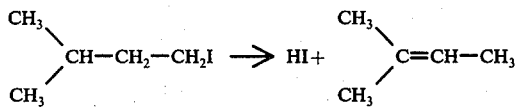

This involves loss of iodide, formation of products of incomplete alkylation of red phosphorus, and reduction of yields of trialkylphosphine oxides. Moreover, when the whole required quantities of alkyl iodide are charged at one time, it becomes impossible to raise the alkylation temperature above the point at which the iodide boils, and the alkylation process is thus carried out at a lower rate and hence requires greater time.

The object of this invention is to increase the yield of the end product, to simplify the process, and to rule out the formation of side products.

In accordance with said and other objects, the invention consists in that trialkylphosphine oxides having the general formula $R_3PO$, where R is an alkyl having from 1 to 16 carbon atoms, are produced by the interaction of red phosphorus with alkyl iodide in the presence of a catalyst with subsequent isolation of the end product, and according to the invention, the process is effected by gradually adding alkyl iodide to the reaction mixture and the process temperature is maintained at 180°–230° C.

The process should preferably be carried out at a temperature of 200°–220° C in the presence of hexaalkyliodophosphoranphosphonium pentaiodide as the catalyst taken in the quantity of 0.1–0.2 g-mole per gram-atom of phosphorus.

It is preferable that red phosphorus and the alkyl iodide should be taken in the molar ratio of 1:3.

The proposed method is carried out as follows.

A mixture of red phosphorus and the catalyst is heated to a temperature of 40°–80° C, then 5–15 ml of alkyl iodide are added and the mixture is heated with stirring to 190°–200° C. The preferred ratio of alkyl iodide to red phosphorus is 3 g-mole per gram-atom respectively. Iodine or hexaalkyliodophosphoranphosphonium pentaiodide can be used as the catalyst. The remaining quantity of alkyl iodide is then added gradually to the reaction mixture within 2–8 hours with stirring at a temperature of 180°–230° C. The preferred process temperature is 200°–220° C and the preferred catalyst — hexaalkyliodophosphoranphosphonium pentaiodide $[R_3P(I)\text{---}PR_3]^+I_5^-$, where R is an alkyl having from 1 to 16 carbon atoms, taken in the quantity of 0.1–0.2 g-mole per gram-atom of phosphorus. The reaction mixture is then cooled to room temperature and the end products isolated by the known methods. The yield of trialkylphosphine oxides is 80–90 percent.

The proposed method simplifies the process of producing lower oxides of (trimethyl-, triethyl-, tripropyl-)phosphines, oxides of phosphines with iso-structure radicals, heteroradical oxides of phosphines, oxides of higher trialkylphosphines, and the duration of the process is shortened to 8–10 hours.

The methods becomes realizable owing to the presence of a constant excess of the catalyst in the reaction of the alkylation of red phosphorus, since the alkyl iodide is not added at one time but is added in portions at high temperature and it immediately takes part in the reaction. The process is autocatalytic, which is otherwise impossible with the processes effected by the known methods. The proposed method rules out any side reactions in which alkyl iodides are dehydrohalogenated which in turn increases the yield of the end products to 80–90 percent against a maximum 70 percent by weight with the methods known in the prior art.

For a better understanding of the invention, the following examples of its practical embodiment are given by way of illustration.

EXAMPLE 1

A four-neck reactor (capacity 500 ml) provided with a reflux condenser, a dropping funnel, a thermometer, a stirrer, and an oil heater, is charged with 15.5 g (0.5 g-atom) of red phosphorus, 25 g of iodine, and 5 g of methyl iodide. The mixture is heated to the point at which the iodide boils (42.5° C), the stirrer is switched on, and the mixture is heated during 30 minutes to a temperature of 200° C. The mixture is then kept at this temperature until the condensate stops dripping off the condenser and brown vapor forms inside the reactor (about 30 minutes). The remaining quantity of methyl iodide is added slowly at a temperature of 200°–220° C at a rate at which the condensate slowly drips off the reflux condenser. The total quantity of methyl iodide used in the reaction is 213 g (1.5 mole). The time during which it is introduced into the reactor is 8 hours. As soon as the temperature of the reaction mixture drops to 60° C methyl alcohol is added gradually to recover iodide as methyl iodide which is removed by distillation and reused in the process.

The end product, trimethylphosphine oxide, is isolated as follows. A 40 percent solution of sodium hydroxide is added to the reaction mixture to precipitate salts of phosphoric acids, and also sodium iodide. The precipitate is separated on a filter, and the filtrate evaporated to dryness. The residue, damp trimethylphosphine oxide, containing admixtures of salts, is sublimed in vacuum. The yield of trimethylphosphine oxide is 34 g, which is 75 percent by weight. The melting point, 136°–138° C.

EXAMPLE 2

The procedure is similar to that described in Example 1. The end product, trimethylphosphine oxide, is isolated as follows. The residue in the reactor that remains after distillation of methyl iodide is kept for an hour in vacuum; and then concentrated (80–96 percent) nitric acid is added gradually with stirring and cooling until iodine stops evolving. The precipitated iodine is separated by filtration, the filtrate is neutralized with soda and sodium hydroxide. The precipitated salts are separated by filtration, washed on the filter with 10–15 ml of methyl alcohol, the filtrate is evaporated to dryness, and the precipitate, damp trimethylphosphine oxide, containing an admixture of salts, is sublimed. The yield of trimethylphosphine oxide is 36 g (80 percent by weight). The melting point of the end product is 136°–138° C.

EXAMPLE 3

The synthesis is effected in an apparatus similar to that described in Example 1. The reaction is charged with 15.5 g (0.5 g-mole) of red phosphorus and 35 g of the product of the alkylation of red phosphorus with ethyl iodide, i.e., hexaethyliodophosphoranphosphonium pentaiodide $[Et_3P(I)—PEt_3]^+I_5^-$. The mixture is stirred and within 30 minutes heated to a temperature of 200° C. Then, at a temperature of 200°–220° C, ethyl iodide is added in drops within 8 hours. The total quantity of ethyl iodide used in the reaction is 235 g (1.5 mole). The reaction mixture is now cooled and processed with ethyl alcohol as described in Example 1. After distillation of ethyl iodide, a 50 percent solution of sodium hydroxide (40 g of 100% NaOH) is added to the reactor at a temperature of 30°–40° C. The reaction mixture is cooled to room temperature, the precipitate is separated on a filter, washed with 20 ml of cold water, and 10–15 g of 100% NaOH are added to the filtrate. The mixture is heated with stirring to dissolve the alkali and the solution is allowed to stand. In 1–2 hours, the organic supernatant is decanted, evaporated in vacuum of 20–30 mm Hg, and the residue is distilled. The triethylphosphine oxide fraction boiling at 111°–114° C (at 8–10 mm Hg) is separated. The yield of the end product is 59 g (88 percent by weight).

EXAMPLE 4

An enamelled iron apparatus (capacity 400 liters) provided with a stirrer, enamelled reflux condenser, a thermometer, and a salt-heating bath, is loaded with a suspension of red phosphorus in isoamyl iodide (22 kg of phosphorus in 25–30 kg of isoamyl iodide) from a 100-liter measuring tank. Now 20 kg of technical iodine are added to the apparatus, which is then sealed, and the stirrer and the reflux condenser are actuated. The mixture is heated in the apparatus to a temperature of 200°–210° C and kept until the condensation process in the reflux condenser stops. The temperature inside the apparatus is now controlled at 200°–220° C and isoamyl iodide is added at a rate at which the reflux condenser is not flooded with the liquid. The total quantity of isoamyl iodide used in the synthesis is 420 kg. As soon as the whole required quantity of isoamyl iodide has been added, the mixture is cooled to 60° C and processed with isoamyl alcohol (to recover iodine as isoamyl iodide) and then with alkali and sodium sulfite. To isolate triisoamylphosphine oxide, 100 liters of benzene are added into the reactor and the product is then washed with sodium sulfite, and water to neutral reaction. After removal of benzene by distillation, crude triisoamylphosphine oxide is distilled in vacuum. The yield of product is 150 kg (83 percent by weight).

EXAMPLe 5

The synthesis is carried out in the apparatus described in Example 4. Heteroradical alkyl iodides (a mixture of $C_{7-9}H_{15-19}I$ iodides in the quantity of 298 kg and isoamyl iodide in the quantity of 123 kg) are used for the synthesis. The quantity of phosphorus is 19.3 kg. The synthesis is effected under conditions specified in Example 4. Phosphine oxide having the formula

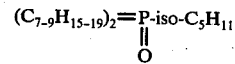

is isolated by vacuum distillation. The yield of product is 175 kg (82.1 percent by weight).

EXAMPLE 6

A three-neck glass reactor of 15-liter capacity, provided with a stirrer, a thermometer, a dropping funnel, and a reflux condenser is charged with 31 g of red phosphorus, 25 g of iodine, and 20 g of cetyl iodide. The mixture is heated with stirring to 200° C and the remaining quantity of cetyl iodide (1056 g) is added within 3 hours at a temperature of 200°–220° C. The mixture is kept at this temperature for another 2 hours and then cooled to 60° C. Then 100 ml of methyl alcohol are added into the reactor, the mixture is boiled for an hour with a reflux condenser, and methyl iodide is distilled (280 g). Now 400 ml of benzene, 200 ml of a 10 percent sodium hydroxide solution, and 150 ml of a saturated sodium sulfite solution are added to the residue in the reactor. The reaction mixture is stirred until its color changes from dark brown to light yellow. The mixture is allowed to stand and the benzene layer is separated and washed with two 200-ml portions of a 10 percent sodium hydroxide solution and saturated solution of sodium sulfite, and finally with water to neutral reaction. Benzene is evaporated, and tricetylphosphine oxide is crystallized from the residue. The yield of tricetylphosphine oxide is 570 g (80 percent by weight). The melting point is 75°–76° C.

We claim:

1. A method for producing a trialkylphosphine oxide having the formula $R_3PO$, where R is an alkyl having from 1 to 16 carbon atoms, comprising reacting red phosphorus with an alkyl iodide where the alkyl group has from 1 to 16 carbon atoms in the presence of a catalyst selected from the group consisting of iodine and hexaalkyliodophosphoranphosphonium pentaiodide, by gradually adding alkyl iodide to the reaction mixture and maintaining the temperature at 180°–230° C, with subsequent isolation of the end product.

2. A method according to claim 1, in which the process is effected at a temperature of 200°–220° C in the presence of hexaalkyliodophosphoranphosphonium pentaiodide as a catalyst taken in the quantity of 0.1–0.2 g-mole per g-atom of phosphorus.

3. A method according to claim 1, in which the red phosphorus and the alkyl iodide are taken in the molar ratio of 1:3.

* * * * *